(12) United States Patent
Watanabe et al.

(10) Patent No.: US 8,771,248 B2
(45) Date of Patent: Jul. 8, 2014

(54) TAMPON

(75) Inventors: Hitoshi Watanabe, Kanonji (JP); Hideki Kondo, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 703 days.

(21) Appl. No.: 12/663,808

(22) PCT Filed: Jun. 10, 2008

(86) PCT No.: PCT/JP2008/060603
§ 371 (c)(1),
(2), (4) Date: Feb. 23, 2010

(87) PCT Pub. No.: WO2008/153020
PCT Pub. Date: Dec. 18, 2008

(65) Prior Publication Data
US 2010/0174262 A1     Jul. 8, 2010

(30) Foreign Application Priority Data

Jun. 11, 2007    (JP) .................................. 2007-153874

(51) Int. Cl.
*A61F 13/20*    (2006.01)
*A61F 13/34*    (2006.01)

(52) U.S. Cl.
CPC ......... *A61F 13/2062* (2013.01); *A61F 13/2065* (2013.01); *A61F 13/34* (2013.01); *Y10S 604/904* (2013.01)
USPC ..................................... 604/385.18; 604/904

(58) Field of Classification Search
CPC ................ A61F 13/2085; A61F 13/34; A61F 13/53418; A61F 13/53427
USPC ......................... 604/385.18, 904; 28/118–120
See application file for complete search history.

(56) References Cited

U.S. PATENT DOCUMENTS 3,369,544 A * 2/1968 Crockford ........................ 604/15
4,642,108 A    2/1987 Sustmann
(Continued)

FOREIGN PATENT DOCUMENTS

JP    54-67334        5/1979
JP    S55-168330 U    12/1980
(Continued)

OTHER PUBLICATIONS

International Search Report mailed Sep. 9, 2008, directed at International Application No. PCT/JP2008/060603; 4 pages.

(Continued)

*Primary Examiner* — Jackie T Ho
*Assistant Examiner* — Peter S Vasat
(74) *Attorney, Agent, or Firm* — Morrison & Foerster LLP

(57) ABSTRACT

It is intended to provide a tampon wherein a string-shaped member is bonded to a cylindrical absorbent in the state of not being exposed on the absorbent surface. A tampon comprising an absorbent (2), which is obtained by molding a sheet member into a cylindrical shape, and a string-shaped member (4) which is bonded to the absorbent (2) and extends from one end of the absorbent (2). The string-shaped member (4) has a first string part which is bonded along the first direction of one face of the sheet member constituting the absorbent (2) and a second string part which extends from the sheet member. A first folding part is formed in one side of the second direction that is perpendicular to the first direction of the first string member, while a second folding part is formed in the other side of the second direction. Owing to this constitution, the absorbent (2) is deformed by bending respectively from the first folding part and the second folding part and thus molded into a cylindrical shape from which the first string part is not exposed.

9 Claims, 16 Drawing Sheets

(56) References Cited

U.S. PATENT DOCUMENTS

| | | | | |
|---|---|---|---|---|
| 5,171,302 | A | * | 12/1992 | Buell ................. 604/385.23 |
| 6,740,070 | B2 | * | 5/2004 | Agyapong et al. ....... 604/385.18 |
| 2003/0225389 | A1 | * | 12/2003 | Cassoni et al. .......... 604/385.18 |
| 2004/0116885 | A1 | * | 6/2004 | Soerens et al. ............... 604/378 |
| 2004/0193131 | A1 | * | 9/2004 | Wada ..................... 604/385.18 |
| 2005/0090794 | A1 | * | 4/2005 | Dyer et al. ............... 604/385.18 |
| 2005/0096619 | A1 | | 5/2005 | Costa |
| 2007/0073257 | A1 | * | 3/2007 | Buck et al. ............... 604/385.18 |

FOREIGN PATENT DOCUMENTS

| | | |
|---|---|---|
| JP | S55-168331 U | 12/1980 |
| JP | 59-82856 | 5/1984 |
| JP | S62-9421 | 1/1987 |
| JP | S62-122631 | 8/1987 |
| JP | 11-155902 | 6/1999 |
| JP | 2001-008964 | 1/2001 |
| JP | 2007-509656 | 4/2007 |
| WO | WO-2005/041833 | 5/2005 |

OTHER PUBLICATIONS

Egyptian Office Action mailed Apr. 4, 2011, directed to Egyptian Patent Application No. 2009121790; 5 pages.

Notice of Reasons for Rejection dated Apr. 11, 2013, directed to Vietnamese Application No. 1-2009-02705; 4 pages.

* cited by examiner

FIG. 5A
FIG. 5B
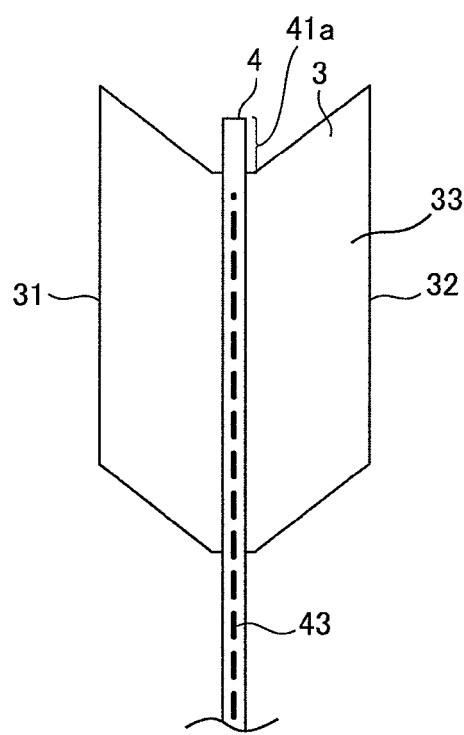
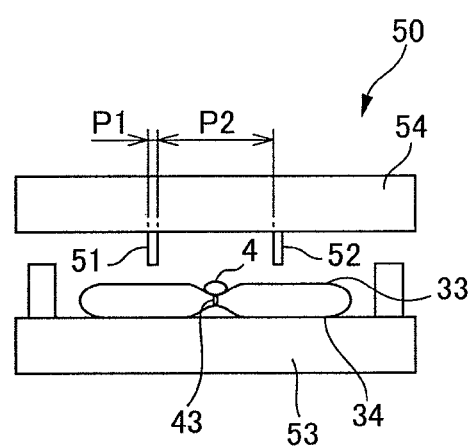

FIG. 6A
FIG. 6B
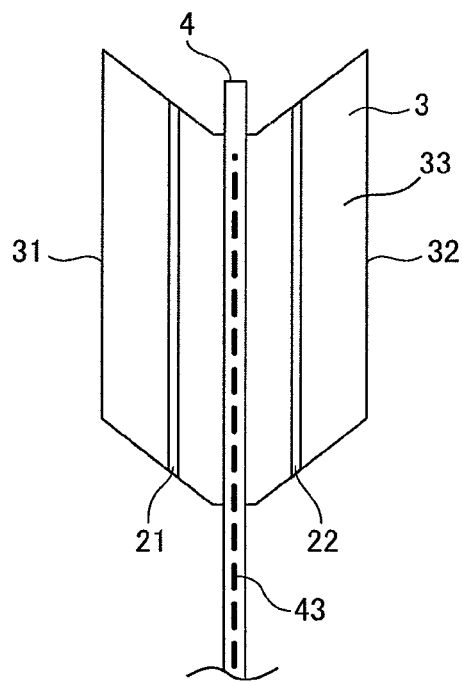
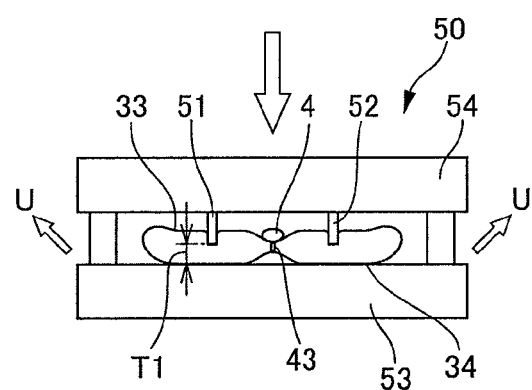

FIG. 10A
FIG. 10B
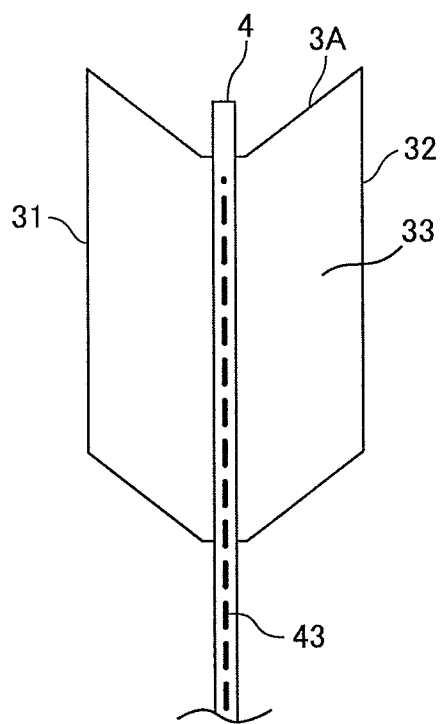
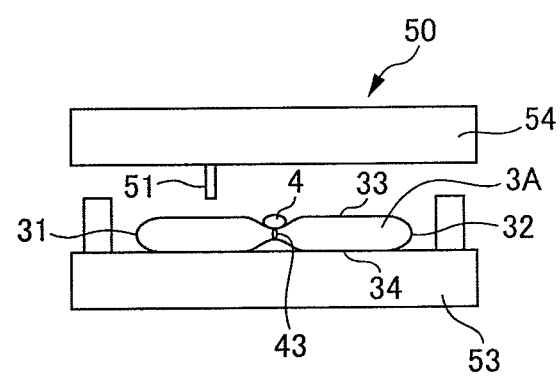

FIG. 11A
FIG. 11B
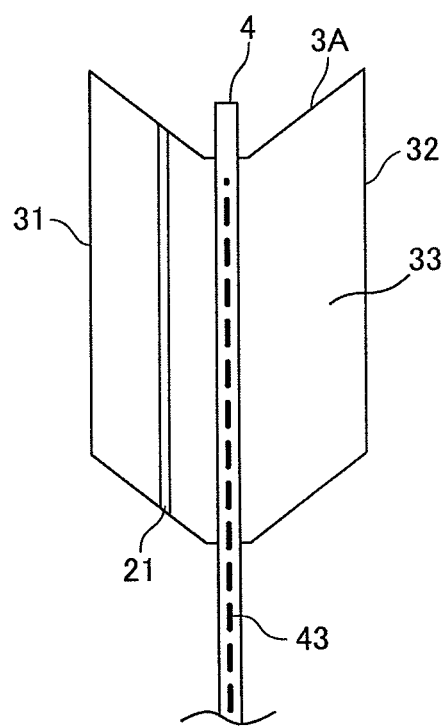
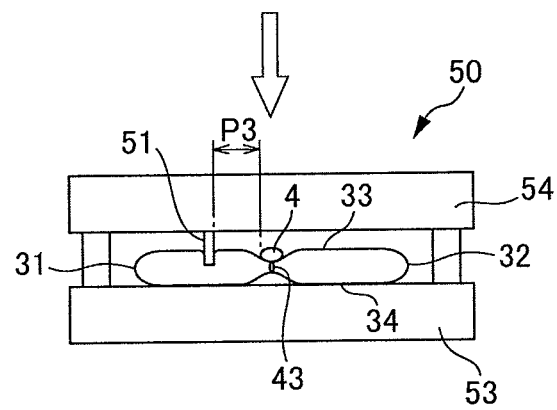

FIG. 12A
FIG. 12B
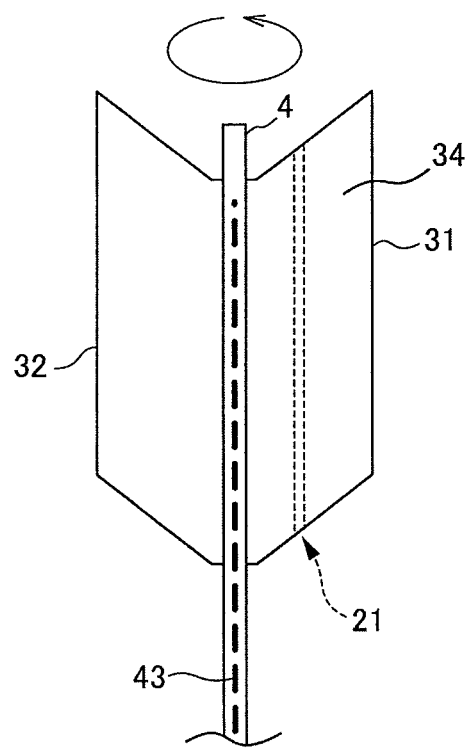
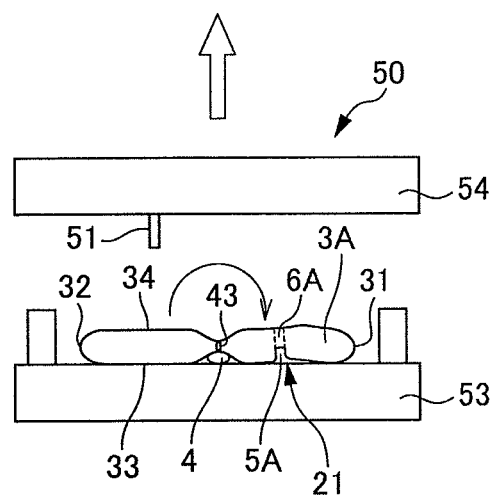

FIG. 13A
FIG. 13B
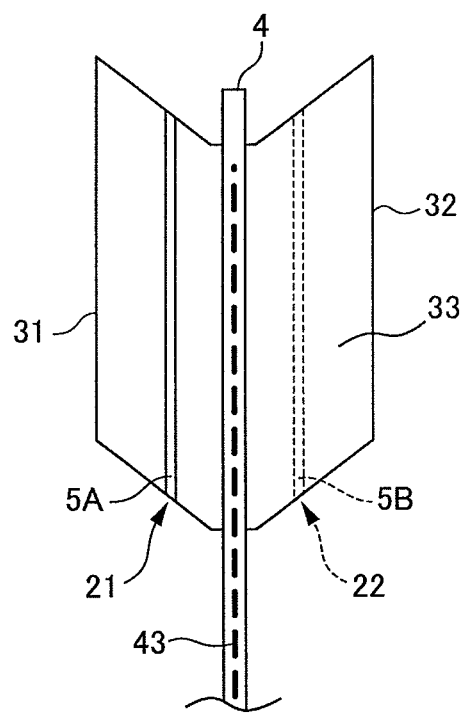
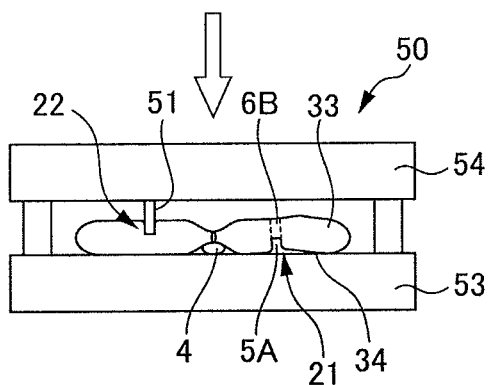

TAMPON

REFERENCE TO RELATED APPLICATION

This application is a national stage application under 35 USC 371 of International Application No. PCT/JP2008/060603, filed Jun. 10, 2008, which claims the priority of Japanese Application No. 2007-153874, filed Jun. 11, 2007, the contents of which prior applications are incorporated herein by reference.

FIELD OF THE INVENTION

The present invention relates to a tampon that is inserted into a vagina and absorbs menstrual blood.

BACKGROUND OF THE INVENTION

Conventionally, a tampon that is molded into a cylindrical shape by compressing a flat absorbent core has been developed as a menstrual tampon. The cylindrical absorbent core is used in a state of being inserted into a vagina and removed therefrom after use. For this reason, the cylindrical absorbent core is provided with a string-shaped member for removal after use. In addition, some tampons are provided with a cylindrical applicator used for inserting the tampon into a vagina.

A tampon has an absorbent core that is limited in size and area for comfortable insertion into a vagina. Various improvements have been made within such limiting conditions, in order to improve absorptive capacity of the absorbent core.

For example, a cylindrical tampon having a concave portion formed on a surface of an absorbent core, in order to improve the absorptive capacity thereof, has been disclosed (Japanese Unexamined Patent Application Publication No. 2001-8964, hereinafter referred to as Patent Document 1). Since the concave portion is formed on the surface of the absorbent core, menstrual blood is absorbed not only from a surface of the absorbent core, but also by the inside of the absorbent core through the concave portion.

However, in such a tampon, there has been no improvement in deforming the absorbent core into a cylindrical shape, in a step of forming the absorbent core into a cylindrical shape. As a result, various molded products have been manufactured that have a cylindrical shape, although the folded shape of the absorbent core is inconsistent.

In a case where the absorbent cores have inconsistent folded shapes, a string-shaped member for removal of the tampon provided in the absorbent core is disposed at variable positions due to folding of the absorbent core. For example, if the string-shaped member is disposed out of a center (a center of gravity in a cross-section) of the cylindrical absorbent core that is molded into a cylindrical shape, a pulling force applied to the string-shaped member is transmitted to a position out of the center (the center of gravity in a cross-section) of the absorbent core when a user tries to remove the absorbent core. As a result, the absorbent core is inclined inside the vagina and may have given an uncomfortable feeling to a user when the user tries to remove the absorbent core. In addition, if the string-shaped member is disposed to be exposed on a surface of the absorbent core, a liquid such as menstrual blood may have leaked through the string-shaped member.

Furthermore, there are products in which the cylindrically-shaped absorbent core is stored in an applicator formed of a resin. At a tip end of the applicator, a part called petals is formed with radial slits that is deformed and opened by the cylindrical absorbent core so as to insert the cylindrical absorbent core into the vagina. Here, in a case where the string-shaped member of a tampon is disposed on a side face of the cylindrical absorbent core, the petals of the applicator may have contacted the string-shaped member and generated friction against a pulling force.

SUMMARY OF THE INVENTION

Problems to be Solved by the Invention

The present invention aims at providing a tampon including an absorbent core that is molded into a cylindrical shape and a string-shaped member bound to the absorbent core in a state of not being exposed on a surface of the absorbent core.

Means for Solving the Problems

The present inventors found that a cylindrically-shaped tampon can be molded as following: in a tampon including an absorbent core obtained by molding a sheet member into a cylindrical shape; and a string-shaped member that is bound to the absorbent core and extends from a first end of the absorbent core, in which the string-shaped member includes the first string portion that is bound to a first surface of the sheet member constituting the absorbent core along a first direction and a second string portion that extends from the sheet member, by forming a first folding portion and a second folding portion across the first string portion, the cylindrically-shaped tampon in which a first string portion is not exposed can be molded, thereby arriving at completing the present invention.

In a first aspect of the present invention, a tampon includes an absorbent core obtained by molding a sheet member into a cylindrical shape; and a string-shaped member that is bound to the absorbent core and extends from a first end of the absorbent core, in which: the string-shaped member includes a first string portion that is bound to a first surface of the sheet member constituting the absorbent core along a first direction, and a second string portion that extends from the sheet member; a first folding portion is formed on one side of the first string portion in a second direction orthogonal to the first direction, and a second folding portion is formed on another side of the first string portion in the second direction; and the absorbent core is deformed so as to fold with the first folding portion and the second folding portion as fold starting points, and molded into a cylindrical shape so as not to expose the first string portion.

According to a second aspect of the present invention, in the tampon as described in the first aspect, the first folding portion and the second folding portion include a first concave portion and a second concave portion, respectively, formed so that a thickness of the sheet member is smaller in thickness than a region adjacent to the first folding portion and the second folding portion, and so as to concave at least one face of the sheet member in a thickness direction thereof.

According to a third aspect of the present invention, in the tampon as described in the second aspect, the first concave portion and the second concave portion are formed on the first surface of the sheet member.

According to a fourth aspect of the present invention, in the tampon as described in the second aspect, the first concave portion is provided on the first surface and the second concave portion is provided on the second surface, which it opposite to the first surface.

According to a fifth aspect of the present invention, in the tampon as described in any one of the first to the fourth aspects, the first folding portion and the second folding portion are formed at a predetermined distance away from the first string portion in the second direction, the predetermined distance being no greater than 0.25 with respect to an overall length of the sheet member in the second direction.

According to a sixth aspect of the present invention, in the tampon according to any one of the first to the fifth aspects, the sheet member includes: a first region that is from the first folding portion to an outer edge close to the first folding portion in the second direction; and a second region that is from the second folding portion to an outer edge close to the second folding portion in the second direction, in which the absorbent core is deformed to be folded at the first folding portion and the second folding portion, and any one of the first region and the second region is disposed to cover the first string portion.

According to a seventh aspect of the present invention, in the tampon as described in the third aspect, the sheet member is formed to have a W-shaped cross-section when viewed from a vertical surface in a longitudinal direction of a cylindrical shape.

According to an eighth aspect of the present invention, in the tampon as described in the fourth aspect, the sheet member is formed to have an N-shaped cross-section when viewed from a vertical surface in the longitudinal direction of the cylindrical shape.

In a ninth aspect of the present invention, a manufacturing method of a cylindrically shaped tampon includes steps of: sewing a sheet member and a string-shaped member that is disposed along a first direction on a first surface of the sheet member; forming a concave portion on both sides of the string-shaped member on the sheet member in a second direction orthogonal to the first direction, and on any one of a first surface of the sheet member and a second surface thereof that is opposite to the first surface; deforming the sheet member so as to fold at the concave portion by moving dies having a concaved curve surface toward each other from both outer edge sides of the sheet member in the second direction; and deforming a region that is from the concave portion to an outer edge of the sheet member thus deformed, along the curved surface of the dies so as to cover a portion of the string-shaped member that is sewn onto the sheet member.

Effects of the Invention

According to the present invention, it is possible to provide a tampon including an absorbent core that is molded into a cylindrical shape and a string-shaped member bound to the absorbent core in a state of not being exposed on a surface of the absorbent core. In addition, it is possible to provide a tampon that gives less uncomfortable feeling to a user in removal of the tampon. Furthermore, a tampon of a stable quality with less variation in shape can be provided.

BRIEF DESCRIPTION OF THE DRAWINGS

FIG. 5A is a plan view of the sheet member according to the first embodiment;
FIG. 5B is a cross-sectional view of the sheet member according to the first embodiment in a state of being placed on a creasing machine;
FIG. 6A is a plan view of the sheet member according to the first embodiment;
FIG. 6B is a cross-sectional view of the sheet member according to the first embodiment in a state of being creased in the creasing machine;
FIG. 10A is a plan view of a sheet member according to a second embodiment;
FIG. 10B is a cross-sectional view of the sheet member according to the second embodiment in a state of being placed on a creasing machine;
FIG. 11A is a plan view of the sheet member according to a second embodiment after forming a first folding portion and a second folding portion;
FIG. 11B is a cross-sectional view of the sheet member according to the second embodiment in a state of being creased in the creasing machine;
FIG. 12A is a plan view of the sheet member on which a first folding portion according to the second embodiment is formed, in a state of being reversed;
FIG. 12B is a cross-sectional view of the sheet member shown in FIG. 12A and the creasing machine;
FIG. 13A is a plan view of the sheet member on which a second folding portion according to the second embodiment is formed;
FIG. 13B is a cross-sectional view of the sheet member shown in FIG. 13A and the creasing machine.

DETAILED DESCRIPTION OF THE INVENTION

Figure 1:
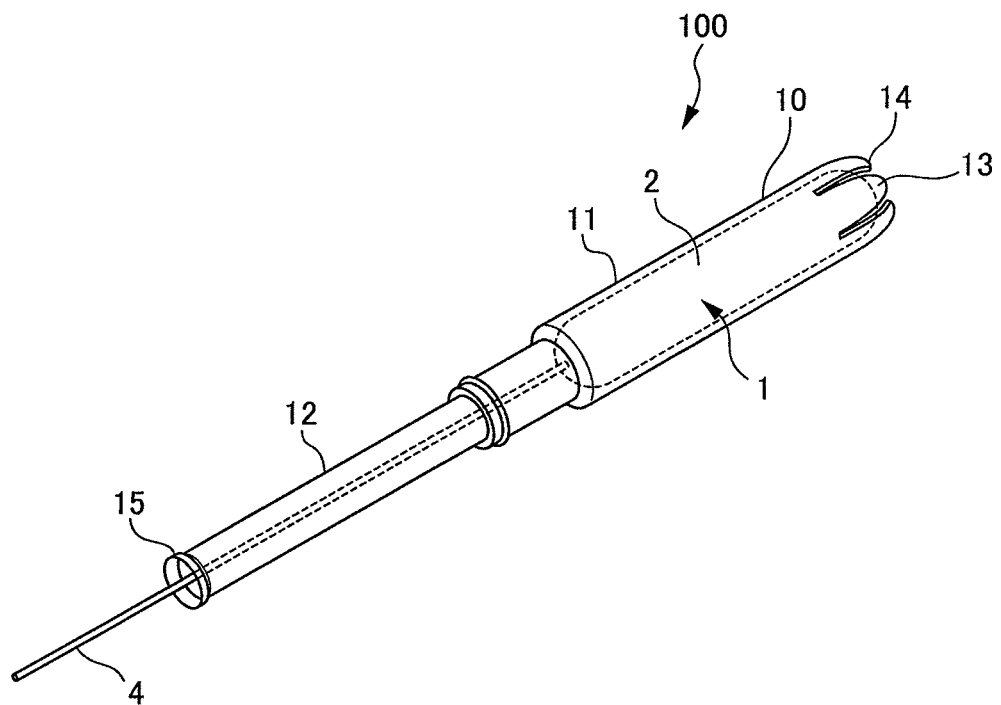
FIG. 1 is a perspective view of a tampon with applicator according to a first embodiment.

Referring to the drawings, embodiments of the present invention are described hereinafter. It should be noted that the present invention and its technical scope are not limited thereto.

1. First Embodiment
1-1. Overall Configuration

The general configuration of the tampon according to the present invention is described with regard to a tampon 100 according to the first embodiment.

FIG. 1 is a perspective view of a tampon with applicator according to a first embodiment. As shown in FIG. 1, the tampon with applicator 100 includes an applicator 10 and a tampon 1.

The applicator 10 is formed of a synthetic resin material and includes an outer cylinder 11 that houses a cylindrically-shaped absorbent core 2 and an inner cylinder 12 that is slidably inserted into the outer cylinder 11 from a rear end portion of the absorbent core 2. In an apex portion 14 of the outer cylinder 11, a plurality of petals 13, which are separated from each other, is integrally formed. A string-shaped member 4 that extends from the rear end portion of the absorbent core 2 is inserted into the inner cylinder 12 and projects rearward from a rear end portion of the inner cylinder 12. The tampon with applicator 100 is used by inserting the outer cylinder 11 of the applicator 10 into a vaginal cavity, and then pushing the inner cylinder into the outer cylinder 11. At this time, the inner cylinder 12 moves the absorbent core 2 inside the outer cylinder 11 toward the apex portion 14 of the outer cylinder 11. Then, the petals 13 at the apex portion 14 of the outer cylinder 11 are deformed to open by the absorbent core 2 thus moved, and the absorbent core 2 is inserted into the vagina by pushing out from the outer cylinder 11.

Figure 2:
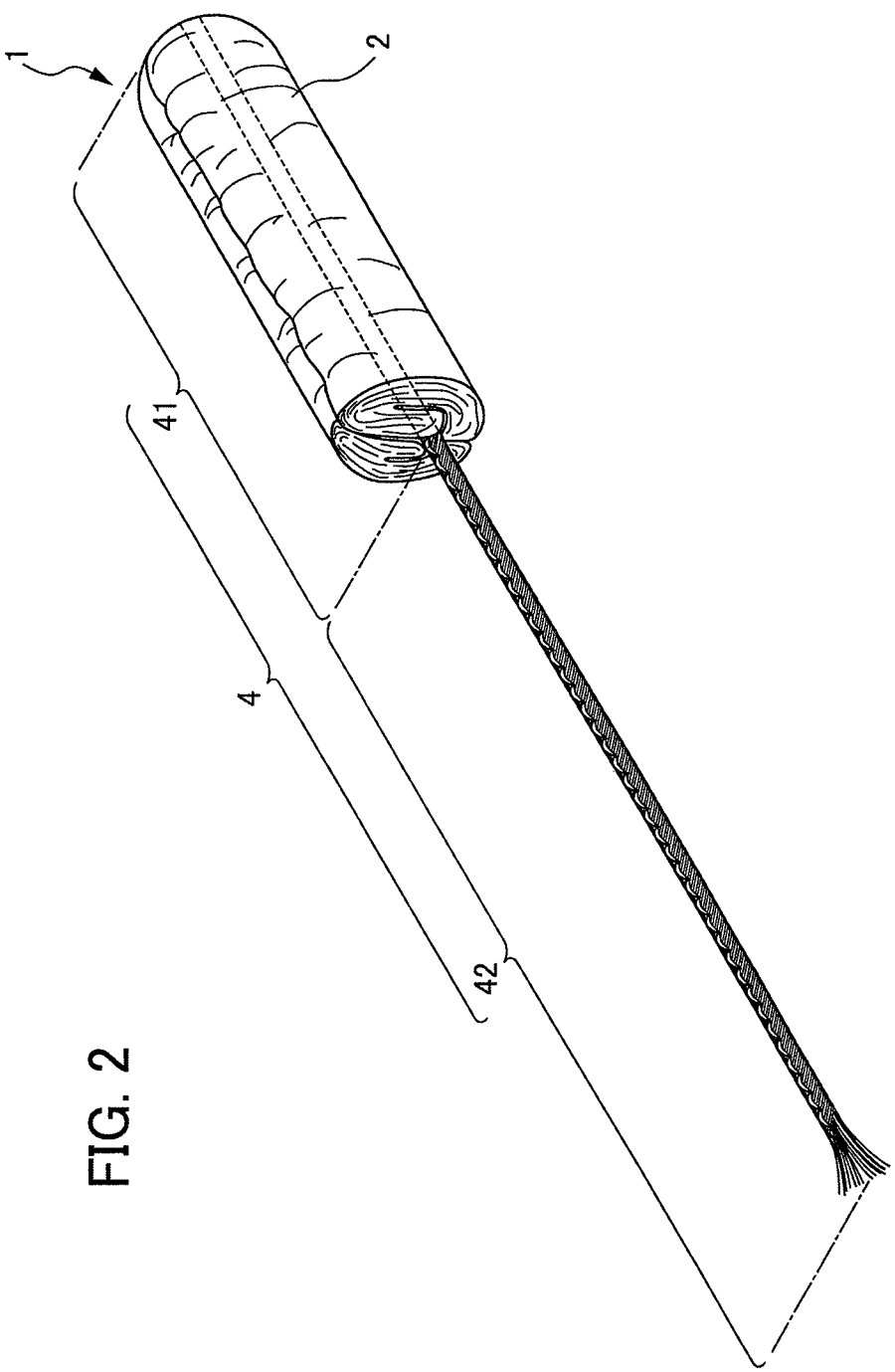
FIG. 2 is a perspective view of an absorbent core according to the first embodiment.
Figure 3:
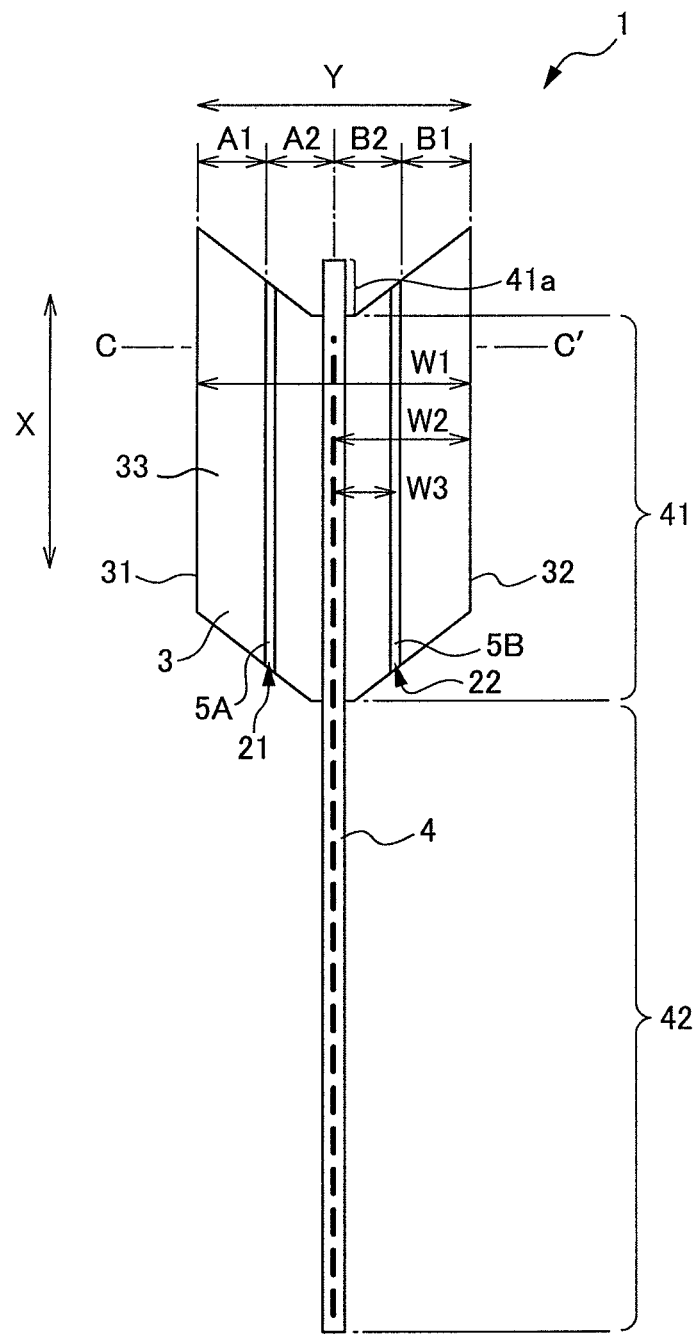
FIG. 3 is a plan view of a sheet member according to the first embodiment.

FIG. 2 is a perspective view of an absorbent core of a tampon according to the first embodiment. As shown in FIG. 2, the tampon 1 includes a cylindrical absorbent core 2 and a string-shaped member 4 which is bound to the absorbent core 2 and of which a first end extends from a rear end of the absorbent core 2. The string-shaped member 4 includes a first string portion 41 and a second string portion 42. The first string portion 41 is disposed in the inside of the absorbent core 2 and the second string portion 42 is disposed on the outside of the absorbent core 2. More specifically, the first string portion 41 is bound to a sheet member 3 constituting the absorbent core 2, in a state of not being exposed from a side face of the cylindrical absorbent core 2. As shown in FIG. 3, a projecting portion 41a projects from the first string portion 41 and extends along an outer edge of the sheet member. The projecting portion 41a is either disposed in the inside of the absorbent core when molding the absorbent core 2, or compressed along a surface of the absorbent core 2.

The absorbent core 2 is obtained by compression-molding of the sheet member 3 into a cylindrical shape. More specifically, the absorbent core 2 is obtained, in a state where the string-shaped member 4 is bound to a first surface of the sheet member 3, by molding the sheet member 3 into a cylindrical shape while deforming the sheet member 3 so as to dispose the string-shaped member 4 on an inner side.

FIG. 3 is a plan view of the absorbent core for the tampon according to the first embodiment, before molding. As shown in FIG. 3, before molding the absorbent core 2 into a cylindrical shape, the tampon 1 includes the sheet member 3 and the string-shaped member 4 that is sewn onto the first surface of the sheet member 3 along a first direction X. The sheet member 3 includes an absorbent portion such as pulp, which is a core of the absorbent core, and a covering sheet that covers the absorbent portion. The string-shaped member 4 has a first string portion 41 that is bound to the sheet member 3, the projecting portion 41a that projects from the first string portion 41, and the second string portion 42 that extends from the sheet member 3.

To a center of the sheet member 3 in a second direction Y that is orthogonal to a first direction X, the first string portion 41 is bound along the first direction. In addition, a first folding portion 21 is formed on a first side of the first string portion 41 in the second direction, while a second folding portion 22 is formed on a second side in the second direction. The absor-bent core 2 is deformed into a cylindrical shape so that the sheet member 3 is folded at the first folding portion 21 and the second folding portion 22 as fold starting points, and so that the first string portion 41 is disposed on the inner side of the absorbent core 2.

1-2. Sheet Member

The sheet member 3 is an absorbent member formed into an arrowhead shape. More specifically, the sheet member 3 is a sheet-like member in which a central portion in the second direction of both outer edges in the first direction has a shape projecting downward in the first direction X, as shown in FIG. 3. The sheet member 3 is obtained by wrapping an absorbent portion consisting of rayon, rayon with an oil solution, or a hydrophilic fiber such as cotton and pulp with a liquid permeable sheet such as a non-woven fabric. The absorbent core 2 is formed by molding the sheet member 3 into a cylindrical shape so that a length in the second direction Y is reduced.

A length of the sheet member 3 in the first direction X can be set accordingly based on a size of the tampon 1 to be manufactured, an absorptive capacity thereof, a shape of a wearer's body and the like. A range of 35 to 40 mm for a small-sized tampon, 60 mm for a medium-sized tampon, 65 mm for a large-sized tampon, 70 to 75 mm and 80 to 90 mm for an extra large-sized tampon can be exemplified.

A width W1 of the sheet member 3 in the second direction Y can also be set accordingly based on a size of the tampon 1 to be manufactured and an absorptive capacity thereof. As the sheet member 3, a sheet member with W1 of 60 m, W2 of 30 mm, and W3 of 15 mm can be exemplified. When W1 is 60 mm, W3 can be in a range of 0.5 mm to 20 mm, preferably in a range of 1 mm to 15 mm, and particularly preferably in a range of 3 to 6 mm. Here, W3, which is a distance between the first string portion 41 and the first folding portion 21, and between the first string portion 41 and the second folding portion 22, needs to be no greater than 0.25 with respect to W1. A case where the distance W3 is greater than 0.25 is not preferable since the first string portion 41 may protrude from a surface of the absorbent core.

In a range of W3 from the first string portion 3, by placing the concave portion inward (closer to the first string portion 41), the absorbent core 2 can be folded more stably. A position of the concave portion 5 is preferably no greater than 0.25 with respect to an overall width W1 of the sheet member 3.

A width of the sheet member can be set accordingly based on a size of the tampon 1 to be manufactured and an absorptive capacity thereof. For example, the width is preferably in a range of 45 to 80 mm.

As described above, the first string portion 41 is bound along the first direction to a center of the sheet member 3 in a second direction Y that is orthogonal to a first direction X. In addition, a first folding portion 21 is formed on one side of the first string portion 41 in the second direction, while a second folding portion 22 is formed on another side in the second direction. In the present embodiment, a direction of the string-shaped member 4 provided on the sheet member 3 is referred to as the first direction, which is shown as the X direction in FIG. 3. A direction orthogonal to the first direction is referred to as the second direction, which is shown as the Y direction in FIG. 3.

As shown in FIG. 3, the sheet member 3 includes a first side edge 31, which is an outer edge closer to the first folding portion, in the second direction from the first folding portion, and a second side edge 32, which is an outer edge closer to the second folding portion, in the second direction from the second folding portion.

W2, which is obtained by equally dividing the overall width W1 of the sheet member 3 in the second direction, is a distance between the first string portion 41 of the string-shaped member 4 and the first side edge 31, or between the first string portion 41 and the second side edge 32, in the second direction. W3, is a distance from the first string portion 41, obtained by substantially equally dividing W2. A range from the first string portion 41 toward the first side edge 31 in the second direction with the distance W3 is shown as A2, and a range from the first string portion 41 toward the second side edge 32 in the second direction with the distance W3 is shown as B2.

In addition, the sheet member 3 includes a first region A1 from the first folding portion 21 to the first side edge 31, and a second region B1 from the second folding portion 22 to the second side edge 32. The first region A1 and the second region B1 are regions that are disposed to cover the first string portion 41 when the sheet member 3 is deformed into a cylindrical shape.

More specifically, the sheet member 3 is deformed to be folded at the first folding portion 21 and the second folding portion 22 as fold starting points, so that the first region A1 and the second region B1 of an top surface 33 covers the first string portion 41. The sheet member 3 is folded to have a W-shaped cross-section when viewed from a vertical face in a longitudinal direction of a cylindrical shape of the tampon 1. In addition, the first side edge 31 and the second side edge 32 of the sheet member 3 face and contact each other, and are deformed to be curled toward the inside of the sheet member 3, thereby molding the sheet member 3 into a cylindrical shape.

Herein, a first surface on which the string-shaped member 4 is provided is referred to as the top surface 33, and a second surface that is on a back surface of the obverse surface 33 is referred to as a back surface 34, for convenience. In addition, a side closer to the string-shaped member 4 in the sheet member 3 is referred to as inside, and a side closer to the first side edge 31 or the second side edge in the sheet member 3 is referred to as outside.

1-3. String-Shaped Member

As shown in FIGS. 2 and 3, the string-shaped member 4 has the first string portion 41 that is bound to the sheet member 3 and the second string portion 42 that is not bound to the sheet member 3. The first string portion 41 is a portion disposed in the inside of the absorbent core 2 that is molded into a cylindrical shape, and the second string portion 42 is a portion extending from a rear end of the absorbent core 2.

The string-shaped member 4 is disposed in a center of the sheet member 3 in the second direction Y along the first direction X. The string-shaped member 4 is only required to be disposed at a position where the string-shaped member 4 is not exposed from the absorbent core 2 in a state where the sheet member 3 is molded into a cylindrical shape of the absorbent core 2, and the position is not particularly limited.

The first string portion 41 of the string-shaped member 4 is sewn onto the top surface 33, which is a first surface of the sheet member 3, with a sewing thread 43. The sewing thread 43 is disposed not only in the first string portion, but also in the second string portion 42.

The string-shaped member 4 and the sewing thread 43 consist of cotton, polyethylene terephthalate (PET), polyethylene (PE), rayon, or a composite fiber thereof. In addition, a fiber constituting the string-shaped member 4 and the sewing thread 43 can be water-repellent finished, in order to prevent menstrual blood from transferring to a user's hand when pulling the string-shaped member 4.

In FIG. 3, as described above, the string-shaped member 4 is bound to the sheet member 3 on a center line along the first direction equally dividing the width W1 of the sheet member 3. In addition, since the sheet member 3 is deformed to be folded at the first folding portion 21 and the second folding portion 22 as fold starting points so that the first region A1 and the second region B1 cover the first string portion 41, the first string portion 41 is disposed in a substantially central portion of a cross-section of the cylindrical absorbent core 2. In other words, by pulling the second string portion 42 that projects from the absorbent core 2, a pulling force is applied to a substantially central portion of the cross-section of the absorbent core 2 and the absorbent core is moved in a removal direction without being inclined.

1-4. Folding Portion 1-4-1. Concave Portion

The first concave portion 5A and the second concave portion 5B are regions formed to be recessed in a thickness direction on the top surface 33 of the sheet member 3. The first concave portion 5A and the second concave portion 5B are formed by a creasing machine 50 having a projection, which is a predetermined convex member.

The first concave portion 5A and the second concave portion 5B are formed on the top surface 33 of the sheet member 3, on both sides in the second direction Y of the first string portion 41. The first folding portion 21 and the second folding portion 22 are each formed with a distance W3 from the first string portion 41. The distance W3 is no greater than 0.25, with 1 being an overall width of the absorbent core 2.

Figure 4:
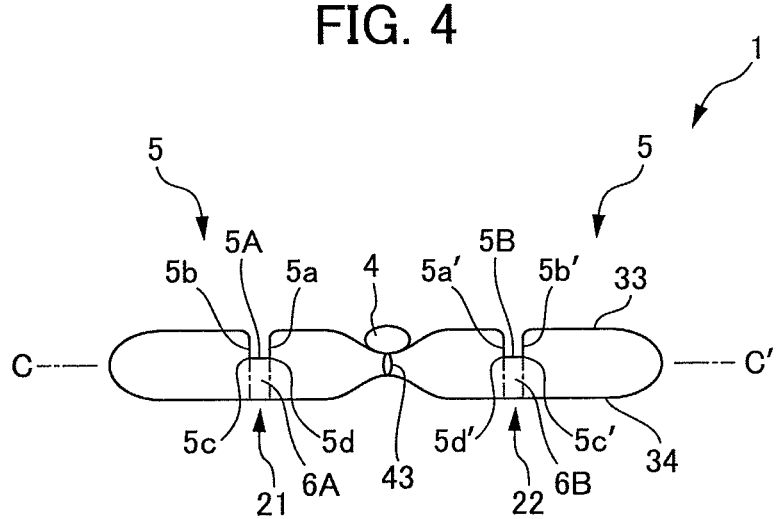
FIG. 4 is a cross-sectional view taken along a line C-C' shown in FIG. 3.

FIG. 4 is a cross-sectional view taken along a line C-C' shown in FIG. 3. A width of the first concave portion 5A and the second concave portion 5B (in other words, a width of the folding portions 21 and 22) is 0.5 to 5 mm, and more preferably 1 to 3 mm. If the width of the first concave portion 5A and the second concave portion 5B is smaller than 0.5 mm, it is difficult to fold the sheet member 3 thereat. If the width of the first concave portion 5A and the second concave portion 5B is greater than 5 mm, the sheet member 3 may be folded at inner angles $5d$ and $5d'$ and outer angles $5c$ and $5c'$ of the concave portions, shown in FIG. 4, and thus deformation thereof may be unstable.

A height of the first concave portion 5A and the second concave portion 5B is preferably in a range of 1 to 3.2 mm. An average thickness of the sheet member in a noncompressed state is preferably in a range of 3.5 to 3.8 mm.

The first concave portion 5A and the second concave portion 5B are formed on the same surface of the sheet member 3. Since the sheet member 3 is deformed to be folded with the first concave portion 5A and the second concave portion 5B facing inside, the first region A1 and the second region B1 are deformed to be folded to cover the first concave portion 5A and the second concave portion 5B. In other words, since the first concave portion 5A and the second concave portion 5B are formed on a surface to which the first string portion 41 is bound, the first region A1 and the second region B1 are deformed to be folded to cover the first string portion 41. In addition, a portion in which the first string portion 41 is bound also acts as a fold starting point, and the sheet member 3 is deformed to have a W-shaped cross-section overall.

Here, if the first concave portion 5A and the second concave portion 5B are disposed symmetrically across the first string portion 41, the sheet member 3 can be stably deformed into a W-shape. However, the first concave portion 5A and the second concave portion 5B are only required to be disposed across the first string portion 41 and not required to be disposed symmetrically across the first string portion 41.

The first concave portion 5A and the second concave portion 5B are required to be disposed on first and second sides in the second direction across the first string portion 41 on the sheet member 3, and there can be a plurality of the first concave portions 5A and a plurality of the second concave portions 5B. If an area of the concave portions in the sheet member is too large, an area of the absorbent core, which is required to form a desired cylindrical shape, is limited, and thus the absorption capacity thereof may be decreased. In addition, since the first concave portion 5A and the second concave portion 5B are formed by compressing the sheet member 3 constituting the absorbent core 2, as the number of the concave portions becomes larger, the density of the absorbent core is increased, whereby the absorption capacity thereof may be decreased. Therefore, the area of the concave portions is preferably configured to such a degree that the absorptive capacity of the absorbent core is not decreased.

1-4-2. Thin-Walled Portion

Thin-walled portions 6A and 6B, along with the abovementioned first concave portion 5A and the second concave portion 5B, constitute the folding portions 21 and 22. The thin-walled portions 6A and 6B are regions formed on a bottom portion of the first concave portion 5A and the second concave portion 5B, continuously in a thickness direction of the sheet member 3. More specifically, the thin-walled portions 6A and 6B are formed, along with the first concave portion 5A and the second concave portion 5B, by compressing the sheet member 3 in the thickness direction, and therefore have a thickness smaller than that of a portion adjacent to the folding portions 21 and 22.

More specifically, the thicknesses of the thin-walled portions 6A and 6B are in a range of 0.05 to 5 mm, and preferably in a range of 0.3 to 0.5 mm. The thickness of the thin-walled portions 6A and 6B is relative to the depth of the concave portion 5 in the folding portions 21 and 22. Here, in a case where the depth of the concave portion increases and the thickness of the absorbent core 2 decreases, the absorptive capacity of the absorbent core 2 may be decreased. The thickness of the thin-walled portions 6A and 6B within the abovementioned range is preferable for maintaining the absorptive capacity of the absorbent core 2 and desirably functioning as a fold starting point.

Since the thin-walled portions 6A and 6B are formed by compressing the sheet member 3, the density thereof is higher than that of the region adjacent to the first folding portion 21 and the second folding portion 22.

Similarly, since the thin-walled portions 6A and 6B are formed by compressing the sheet member 3, the stiffness thereof is also higher than that of the region adjacent to the first folding portion 21 and the second folding portion 22.

Here, basis weight of the thin-walled portions 6A and 6B (folding portions 21 and 22) can be adjusted to be lower than that of the region adjacent to the thin-walled portions 6A and 6B (folding portions 21 and 22). By making the basis weight of the thin-walled portions 6A and 6B (folding portions 21 and 22) lower than other regions, the thin-walled portions 6A and 6B (folding portions 21 and 22) become easier to fold.

The basis weight of the thin-walled portions 6A and 6B (folding portions 21 and 22) can be accordingly set based on a size and absorptive capacity of the tampon 1 to be manufactured. As the basis weight, 590 g/m$^2$ and 880 g/m$^2$ can be exemplified for a small-sized tampon and a medium-sized tampon, respectively. The basis weight of the thin-walled portions 6A and 6B (folding portions 21 and 22) lower than 20 g/m$^2$ is not preferable since the thin-walled portions may be torn while molding into the cylindrical shape.

In a case where a lower basis weight is preferred, as the basis weight of the thin-walled portions 6A and 6B (folding portions 21 and 22), a range of 20 to 300 g/m$^2$ and a range of 20 to 400 g/m$^2$ can be exemplified for the small-sized tampon and the medium-sized tampon in the abovementioned example, respectively. The abovementioned upper limit can be obtained by dividing the basis weight of the absorbent core in the sheet member into two, and the lower limit can be obtained by dividing the basis weight of the covering sheet in the sheet member into two.

It should be noted that the folding portions 21 and 22 can be provided only by lowering the basis weight, without forming concave portions using the creasing machine 50 and the like.

1-4-3. Forming of Folding Portions

Figure 7:
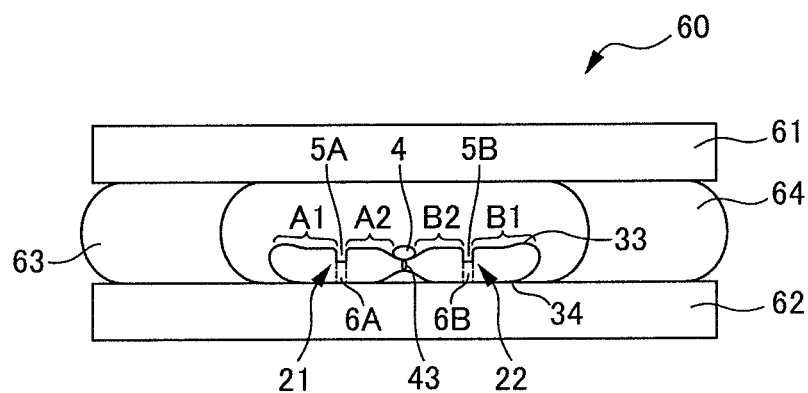
FIG. 7 is a cross-sectional view of the sheet member according to the first embodiment in a state of being placed on a press machine.
Figure 8:
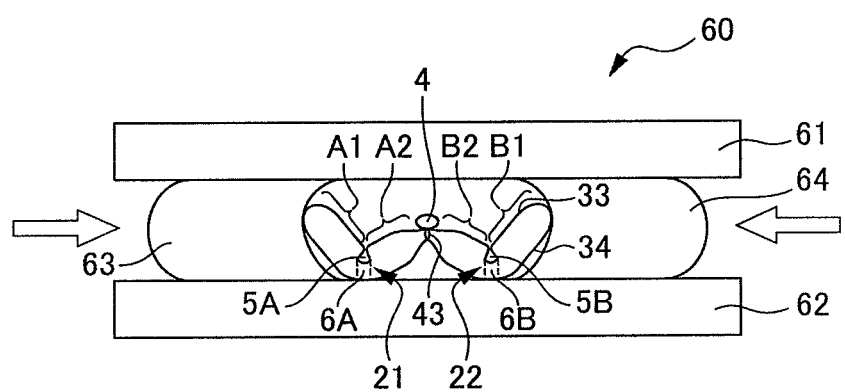
FIG. 8 is a cross-sectional view of the sheet member shown in FIG. 7 in a state of being compressed by the press machine.
Figure 9:
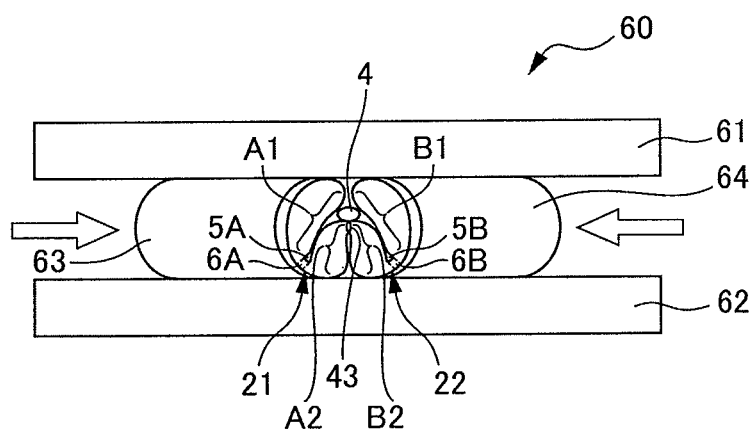
FIG. 9 is a cross-sectional view of the sheet member shown in FIG. 8 in a state of being further compressed.

FIG. 5A is a plan view of the sheet member according to the first embodiment before forming the first folding portion and the second folding portion. FIG. 5B is a cross-sectional view of the sheet member in a state of being placed on a creasing machine. FIG. 6A is a plan view of the sheet member after forming the first folding portion and the second folding portion. FIG. 6B is a cross-sectional view of the sheet member in a state of being creased in the creasing machine. FIG. 7 is a cross-sectional view of the sheet member according to the first embodiment in a state of being placed on a press machine. FIG. 8 is a cross-sectional view of the sheet member shown in FIG. 7 in a state of being compressed by the press machine. FIG. 9 is a cross-sectional view of the sheet member shown in FIG. 8 in a state of being further compressed.

The forming process of the folding portions 21 and 22 is described hereinafter with reference to FIGS. 5A to 9. First, as shown in FIG. 5B, the sheet member 3 is placed on a base 53 of the creasing machine 50. More specifically, the sheet member 3 is placed such that the top surface 33, to which the string-shaped member 4 is bonded, faces the projections 51 and 52 and the back surface 34 faces the base 53.

Figure 20:
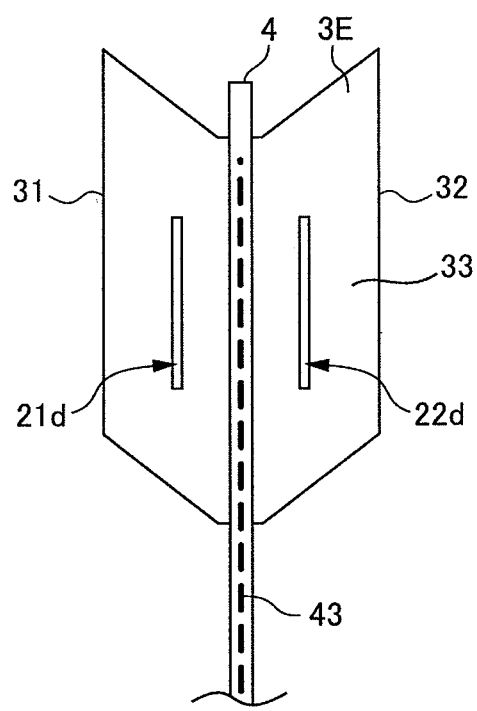
FIG. 20 is a diagram illustrating a modification of a sheet member according to another embodiment.
Figure 21:
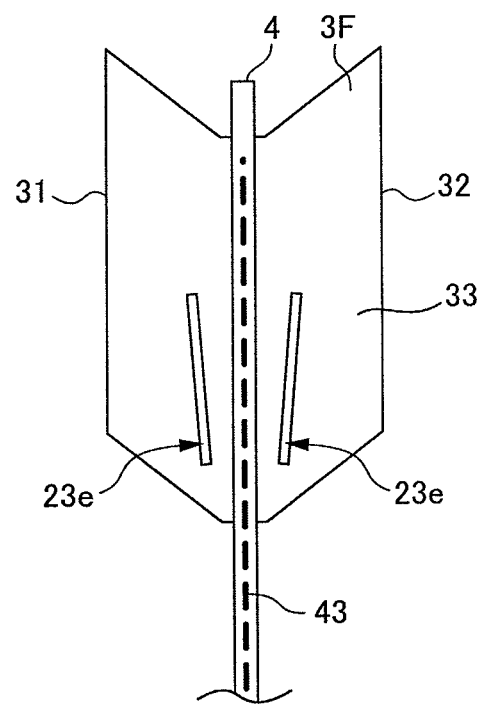
FIG. 21 is a diagram illustrating a modification of a sheet member according to another embodiment.

The creasing machine 50 includes the base 53 on which the sheet member 3 is placed and a creasing member 54 that is disposed to face the base 53, and is provided with the projections 51 and 52 for forming the concave portion. The projections 51 and 52 are formed to project toward the base 53 and to extend in the first direction of the sheet member 3. Here, a shape of the projections 51 and 52 corresponds to a shape of the concave portion. As the shape of the projections, a shape that can form a curved concave portion or a dotted concave portion can be exemplified. Alternatively, as shown in FIGS. 20 and 21 described later, the concave portion can be provided not entirely in a length of the sheet member 3 in the first direction, but partially in the length of the sheet member 3 in the first direction, for example, in the vicinity of a center thereof or the second string portion.

A width P1 of the projections 51 and 52 is set based on a width of the concave portions 5A and 5B. A distance P2 between the projections 51 and 52 is set based on a distance between the first concave portion 5A and the second concave portion 5B. A height P4 of the projections 51 and 52 is set based on a depth of the first concave portion 5A and the second concave portion 5B. For example, in a case where a length W1 of the sheet member 3 in the second direction Y is 44 mm and W3 is 11 mm, the distance P2 is set to be no greater than 22 mm. In addition, in a case where the depth of the concave portions 5A and 5B is 1 mm, the height P4 is set to be 1 mm.

Subsequently, as shown in FIG. 6B, the creasing member 54 in the creasing machine 50 is moved to a side of the base 53, and the first concave portion 5A and the second concave portion 5B are formed by way of the projections 51 and 52. The creasing member 54 is moved to be pushed down toward the back surface 34 (hereinafter referred to as downward) in a state of being in contact with the top surface 33 (hereinafter referred to as upward) of the sheet member 3. By compressing or displacing fibers constituting the sheet member 3 by pressing a predetermined portion on the top surface 33 of the sheet member 3 with the projections 51 and 52, the first concave portion 5A and the second concave portion 5B are formed as shown in FIG. 6A.

This step of forming the first concave portion 5A and the second concave portion 5B using the creasing machine 50 is carried out at ambient temperature. Furthermore, a descent position of the creasing member 54 is adjusted so that a thickness T1 of the sheet member 3 from the back surface 34 to a bottom face of the first concave portion 5A and the second concave portion 5B (thin-walled portions 6A and 6B) is in a range of 0.05 to 0.5 mm, and more preferably in a range of 0.3 to 0.5 mm. The thin-walled portions 6A and 6B having a thickness smaller than 0.05 mm, the sheet member 3 may be torn therefrom.

Here, as shown in FIG. 6B, when the first concave portion 5A and the second concave portion 5B are being formed by the creasing machine 50, the sheet member 3 is deformed such that the first side edge 31 and the second side edge 32 move upward in a thickness direction (a direction of an arrow U in FIG. 6B) of the sheet member 3 (the thin-walled portion). In such a configuration, when the sheet member 3 is compressed from both side edges in a molding step (described later), the sheet member 3 can be more easily deformed into a W-shape or M-shape (described later) since the both side edges 31 and 32 can move upward more easily.

1-4-4. Molding

A process for molding the sheet member 3 is described with reference to FIGS. 7 to 9. First, as shown in FIG. 7, the sheet member 3 with the first concave portion 5A and the second concave portion 5B being formed is placed inside a press machine 60. The press machine 60 includes flat plates 61 and 62 that are disposed to face each other in a vertical direction in FIG. 7 and press members 63 and 64 that are horizontally movable and disposed between the flat plates 61 and 62 so as to face each other in a horizontal direction. The flat plates 61 and 62 restrict a movement direction of the press members 63 and 64 and limits a direction of deformation of the sheet member 3. The press members 63 and 64 are formed in a curved shape in which faces facing each other are convex outward in a horizontal direction. In addition, as described above, the press members 63 and 64 are formed to be horizontally movable so as to approach each other.

Subsequently, as shown in FIG. 8, the press members 63 and 64 of the press machine 60 are moved to a side on which the sheet member 3 is disposed. In other words, the press members 63 and 64 are moved so that a distance therebetween becomes smaller. By thus moving the press members 63 and 64, the sheet member 3 that is disposed therebetween is deformed to be narrower in width. More specifically, as shown in FIG. 8, the press members 63 and 64 applies an inward pressing force in the width direction to the sheet member 3, thereby deforming the sheet member 3 such that both side edges 31 and 32 move upward in the vertical direction. In other words, the first region A1 and the second region B1 are deformed to incline toward the top surface side, with the first folding portion 21 and the second folding portion 22 as folding starting points. In addition, a position at which the first string portion 41 is bound to the sheet member 3 also acts as a folding starting point; however, movement of the position is restricted by the flat plate 62 that is disposed below in the vertical direction to an upward movement in the vertical direction. As a result, the sheet member 3 is deformed to have a W-shaped cross-section.

Then, the press members 63 and 64 are further moved to approach each other. By moving the press members 63 and 64 to approach each other, the sheet member 3 is deformed to be narrower in width of a W-shape in FIG. 8, and the first region A1 and the second region B1 are deformed to cover the first string portion 41. More specifically, the first region A1 and the second region B1 are deformed inward to face or overlap each other vertically above the first string portion, and disposed to cover the first string portion 41. The sheet member 3 is thus compression-molded into a cylindrical shape. The first string portion 41 is disposed in a substantially central portion in a cross-section thereof.

Similarly, when the press members 63 and 64 apply an inward pressing force in the width direction to the sheet member 3, the sheet member may move to cause a position where the first string portion 41 is bound to the sheet member 3 to swell upward. Here, since a movement of the position where the first string portion 41 is bound is restricted by the flat plate 61 that is disposed above in the vertical direction, the position is moved downward in the vertical direction if an inward force in the width direction is continuously applied to the sheet member 3. In addition, the sheet member 3 is deformed such that the first region A1 and the second region B1 incline toward the back surface side, with the first folding portion 21 and the second folding portion 22 as starting points. As a result, the sheet member 3 is deformed to have an M-shaped cross-section.

By moving the press members 63 and 64 to approach each other, the sheet member 3 is deformed to be narrower in width of the M-shape thus formed, and a region A2 and a region B2 are deformed to cover the first string portion 41. More specifically, the region A2 and the region B2 are deformed inward to face or overlap each other vertically below the first string portion, and disposed to cover the first string portion 41. The sheet member 3 is thus compression-molded into a cylindrical shape. The first string portion 41 is disposed in a substantially central portion in a cross-section thereof.

According to the first embodiment, by forming the first folding portion and the second folding portion on the sheet member 3 that is to be molded into the absorbent core 2 of the tampon 1, the sheet member 3 can be stably folded into a W-shape (M-shape). Since the sheet member is folded into a W-shape (M-shape), the sheet member is deformed to cover the first string portion 41 of the string-shaped member 4. The string-shaped member 4 is disposed in a substantially central portion of the absorbent core 2, as being covered by the sheet member 3.

Since the string-shaped member 4 is disposed in a substantially central portion of the absorbent core 2, when a user pulls the string-shaped member 4 for removal of a tampon from the vagina, a pulling force is transmitted to the substantially central portion in a cross-section of the absorbent core 2. Therefore, the tampon 1 does not incline in the vagina and give an unbalanced force to the vaginal wall. As a result, the tampon gives a less uncomfortable feeling to the vaginal wall during removal of the tampon.

The first embodiment is a tampon with applicator, the applicator being provided with radial slits called petals in an apex portion 14 thereof, which is tucked and formed into a rounded shape. Here, since the string-shaped member is disposed in a substantially central portion of the cylindrical shape of the tampon, the string-shaped member does not contact the apex portion 14 in pushing out and inserting the tampon 1 into the vagina. The applicator does not contact the surface unevenness of the string-shaped member and allows a user to insert the tampon without friction due to the unevenness, while giving a less uncomfortable feeling to the vaginal wall.

In addition, in the tampon 1 according to the first embodiment, the string-shaped member is bound to the absorbent core 2 without being exposed to a surface of the absorbent core 2. This can inhibit leakage of a liquid such as menstrual blood running along the string-shaped member.

Similarly, as described above, in the tampon 1 according to the first embodiment, the string-shaped member is bound to the absorbent core 2 without being exposed to a surface of the absorbent core 2. This can provide a tampon 1 that is superior in quality. This is because the string-shaped member not being exposed to a surface of the absorbent core 2 becomes harder to break. In addition, in manufacturing of such a tampon, a ratio of defective products can be decreased and manufacturing yield can be improved. In other words, the tampon is also superior from the perspective of manufacturing cost.

2. Second Embodiment

2-1. Overall Configuration

A tampon 1A according to the second embodiment is different from the first embodiment in that the first folding portion 21 is provided on the top surface 33 of a sheet member 3A and the second folding portion 22 is provided on the back surface 34 of the sheet member 3A. As a result, the sheet member 3 is not a W-shape or M-shape, but rather folded into an N-shape. In the second embodiment, only differences from the first embodiment are described and descriptions for parts that are identical to that described in the first embodiment are omitted.

2-2. Sheet Member

The sheet member 3A for the tampon 1A according to the second embodiment is deformed to be folded at the first folding portion 21 and the second folding portion 22 as fold starting points, so that any one of the first region A1 and the second region B1 of the top surface 33 covers the string-shaped member. The sheet member 3 is folded to have an N-shaped cross-section when viewed from a vertical face in a longitudinal direction of a cylindrical shape of the tampon 1.

On the sheet member 3A, the first folding portion 21 and the second folding portion 22 are provided alternately on the top surface 33 and on the back surface 34. One of the first region A1 and the second region B1 is deformed to cover the first string portion 41. The other of the first region A1 and the second region B1, which is not deformed to cover the first string portion 41, is deformed to be folded to an opposite side thereto, across the regions A1 and B2 in the vicinity of the first string portion of the sheet member 3A. In such a state, the sheet member 3A is compression-molded into a cylindrical shape.

2-3. Folding Portion

Figure 14:
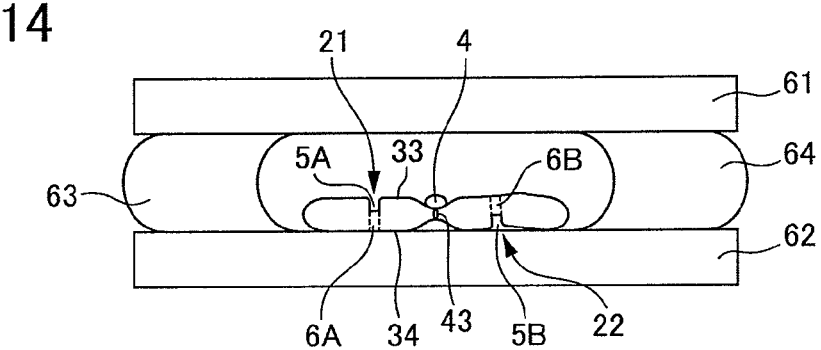
FIG. 14 is a cross-sectional view of the sheet member according to the second embodiment in a state of being placed on a press machine.

The sheet member 3A according to the second embodiment is shown in FIG. 14. The first folding portion 21 is formed on the top surface 33 of the sheet member 3A and the second folding portion 22 is formed on the back surface 34 thereof. The first concave portion 5A and the second concave portion 5B are formed on one side on the top surface 33 and another side on the back surface 34, across the first string portion 41 in the second direction Y. The first concave portion 5A and the second concave portion 5B are each formed with a distance of W3 from the first string portion 41. The first concave portion 5A and the second concave portion 5B, and the thin-walled portions 6A and 6B that are disposed on a bottom portion thereof, constitute the folding portions 21 and 22, respectively.

2-3-1. Concave Portions

The first concave portion 5A and the second concave portion 5B are regions formed to be recessed in a thickness direction on the top surface 33 and the back surface 34 of the sheet member 3. The first concave portion 5A and the second concave portion 5B are formed by a creasing machine 50 having a projection, which is a predetermined convex member.

The first concave portion 5A and the second concave portion 5B are formed on the first side on the top surface 33 and on the second side on the back surface 34, respectively, across the first string portion 41 in the second direction Y. The first folding portion 21 and the second folding portion 22 are each formed to be separated with a distance of W3 from the first string portion 41. The distance W3 is no greater than 0.25 relative to the overall length, with 1 being an overall length of the width of the absorbent core 2.

The size of the first concave portion 5A and the second concave portion 5B is similar to that in the first embodiment. In addition, the size of the thin-walled portions 6A and 6B, which constitute the folding portions 21 and 22 along with the first concave portion 5A and the second concave portion 5B, is also similar to that in the first embodiment.

The first concave portion 5A and the second concave portion 5B are formed on different surfaces of the sheet member 3. Since the sheet member 3A is deformed to be folded with the concave portion facing inside, the first region A1 or the second region B1 is deformed to be folded to cover the first concave portion 5A or the second concave portion 5B. One of the first region A1 and the second region B1 is deformed to cover the first string portion 41. The other of the first region A1 and the second region B1, which is not deformed to cover the first string portion 41, is deformed to be folded to an opposite side thereto, across the regions A1 and B2 in the vicinity of the first string portion of the sheet member 3A.

In other words, the first concave portion 5A is formed on the top surface 33 to which the first string portion 41 is bound, and the second concave portion 5B is formed on the back surface 34 that is opposite to the face to which the first string portion 41 is bound. The first region A1 is deformed to be folded in a direction to cover the first string portion 41. The second region B1 is folded in an opposite direction to the first region A1, and deformed to be folded to an opposite side thereto, across the regions A1 and B2 in the vicinity of the first string portion 41 of the sheet member 3A. As a result, the sheet member 3A according to the second embodiment is folded to have an N-shaped cross-section when viewed from a vertical surface in a longitudinal direction of a cylindrical shape of the tampon 1.

2-3-2. Forming of Folding Portions

The forming process of the folding portions 21 and 22 is described hereinafter with reference to FIGS. 10A to 16.

FIG. 10A is a plan view of the sheet member according to the second embodiment before forming the first folding portion and the second folding portion. FIG. 10B is a cross-sectional view of the sheet member in a state of being placed on a creasing machine. First, as shown in FIG. 10B, the sheet member 3 is placed on a base 53 of the creasing machine 50. More specifically, the sheet member 3 is placed such that the top surface, to which the first string portion 41 is bonded, faces the projection 51 of the creasing machine 50 and the back surface faces the base 53.

The creasing machine 50 includes the base 53 on which the sheet member 3 is placed, and a creasing member 54 that is disposed to face the base 53 and provided with the projection 51 for forming the concave portion. The projection 51 is formed to project toward the base 53 and to extend in the first direction of the sheet member 3. Here, a shape of the projection 51 corresponds to a shape of the concave portion. As the shape of the projections, a shape that can form a curved concave portion or a dotted concave portion can be exemplified. Alternatively, as shown in FIGS. 20 and 21 described later, the concave portion can be in a shape that can be provided not entirely in a length of the sheet member 3 in the first direction, but partially in the length of the sheet member 3 in the first direction, for example, in the vicinity of a center thereof or the second string portion.

FIG. 11A is a plan view of the sheet member after forming the first folding portion and the second folding portion. FIG. 11B is a cross-sectional view of the sheet member in a state of being creased in the creasing machine. As shown in FIG. 11B, regarding a positional relationship between the projection 51 and the sheet member 3A, in a case where the sheet member 3A is placed on the base 53, a distance P3 between the first string portion 41 and an inner side of the projection 51 is set based on a distance between an inner side of the first concave portion 5A and an inner side of the second concave portion 5B in the second direction Y. In addition, a height P4 of the projection 51 is set based on a depth of the concave portions 5A and 5B. For example, in a case where a length W1 of the sheet member 3 in the second direction Y is 44 mm and W3 is 11 mm, the distance P3 is set to be no greater than 11 mm. In addition, in a case where the depth of the concave portions 5A and 5B is 1 mm, the height P4 is set to be 1 mm.

Subsequently, the creasing member 54 in the creasing machine 50 is moved to a side of the base 53, and the first concave portion 5A is formed by way of the projection 51. The creasing member 54 is moved to be pushed down toward a face of the sheet member 3A to which the first string portion 41 is not bound, in a state of being in contact with a face of the sheet member 3A to which the first string portion 41 is bound. By displacing fibers constituting the sheet member 3A by pressing a predetermined portion on the top surface of the sheet member 3A with the projection 51, the first concave portion 5A is formed as shown in FIG. 11A.

FIG. 12A is a plan view of the sheet member on which a first folding portion is formed, in a state of being reversed. FIG. 12B is a cross-sectional view of the sheet member shown in FIG. 12A and the creasing machine. Thereafter, as shown in FIGS. 12A and 12B, the sheet member 3A is reversed, the absorbent core is placed on the base 53 such that the face 33 to which the first string portion 41 is bound contacts the base 53, and the face 34 to which the first string portion 41 is not bound faces the projection 51. Since the absorbent core is reversed, a concave portion is not yet formed on the face of the sheet member facing the projection. By further moving down the creasing member 54 toward the base 53, as shown in FIGS. 13A and 13B, the second concave portion 5B is formed on the face 34 of the sheet member 3A to which the first string portion 41 is not bound, to be mutually alternating with the concave portion 5A formed on the face of the sheet member 3A to which the first string portion 41 is bound.

This step of forming the first concave portion 5A and the second concave portion 5B using the creasing member 54 is carried out at ambient temperature. Furthermore, a descent position of the creasing member 54 is adjusted so that the thickness T1 of the thin-walled portions 6A and 6B is in a range of 0.05 to 0.5 mm, and more preferably in a range of 0.3 to 0.5 mm. The thin-walled portions having a thickness smaller than 0.05 mm, the sheet member 3 may be torn therefrom.

FIG. 13A is a plan view of the sheet member on which a second folding portion is formed. FIG. 13B is a cross-sectional view of the sheet member shown in FIG. 13A and the creasing machine. Here, as shown in FIG. 13B, when the first concave portion 5A and the second concave portion 5B are being formed by the creasing machine 50, the sheet member 3A is deformed such that the first side edge 31 and the second side edge 32 move in a thickness direction of the sheet member 3, which is opposite to a moving direction of the projection 51. This is because, in response to a pressing force from the projection 51, the sheet member rebounds in an opposite direction to the projection 51. In such a configuration, when the sheet member 3 is compressed from both side edges in a molding step (described later), the sheet member 3 can be more easily deformed into an N-shape (described later), since the both side edges 31 and 32 can move in different directions more easily.

2-3-3. Molding

Figure 15:
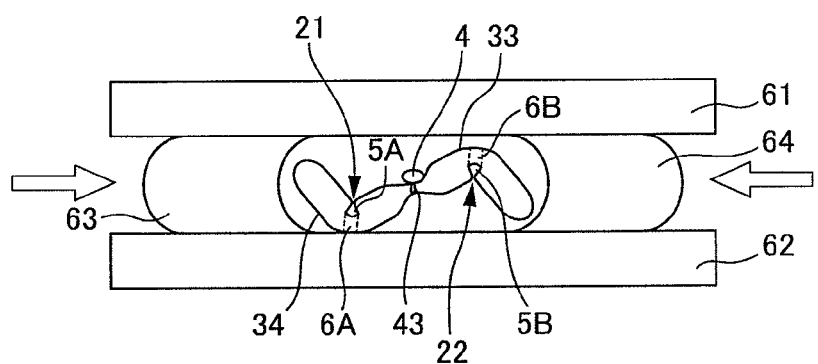
FIG. 15 is a cross-sectional view of the sheet member shown in FIG. 14 in a state of being compressed by the press machine.
Figure 16:
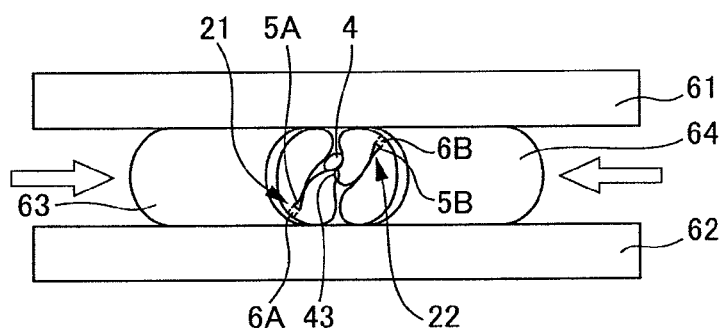
FIG. 16 is a cross-sectional view of the sheet member shown in FIG. 15 in a state of being further compressed.

FIG. 14 is a cross-sectional view of the sheet member according to the second embodiment in a state of being placed on a press machine. FIG. 15 is a cross-sectional view of the sheet member shown in FIG. 14 in a state of being compressed by the press machine. FIG. 16 is a cross-sectional view of the sheet member shown in FIG. 15 in a state of being further compressed. The process for molding the sheet member 3A is described with reference to FIGS. 14 to 16.

First, as shown in FIG. 14, the sheet member 3 with the first concave portion 5A and the second concave portion 5B being formed is placed inside a press machine 60.

The press machine 60 includes flat plates 61 and 62 that are disposed to face each other in a vertical direction in FIG. 14, and press members 63 and 64 that are horizontally movable and disposed between the flat plates 61 and 62 so as to face each other in a horizontal direction. The flat plates 61 and 62 restrict a movement direction of the press members 63 and 64, and limit a deformation direction of the sheet member 3A. The press members 63 and 64 are formed in a curved shape in which faces facing each other are convex outward. In addition, the press members 63 and 64 are formed to be horizontally movable so as to approach each other.

Subsequently, as shown in FIG. 15, the press members 63 and 64 of the press machine 60 are moved to a side on which the sheet member 3A is disposed. In other words, the press members 63 and 64 are moved so that a distance therebetween becomes smaller. By thus moving the press members 63 and 64, the sheet member 3A that is disposed therebetween is deformed to be narrower in width. More specifically, as shown in FIG. 15, the press members 63 and 64 apply an inward pressing force in the width direction to the sheet member 3A, thereby deforming the sheet member with the face, on which the folding portions 21 and 22 are provided, facing inside.

For example, the first side edge 31 of the sheet member 3A is deformed to move upward in the vertical direction. In other words, the first region A1 is deformed to incline toward the face 33 to which the first string portion 41 is bound, with the first folding portion 21 as a starting point.

On the other hand, for example, the second side edge 32 is deformed to move downward in the vertical direction, with the second folding portion 22 as a starting point. In other words, the second region B1 is deformed to incline toward the face 34 to which the first string portion 41 is not bound, with the second folding portion 22 as a starting point. As a result, the sheet member 3 is deformed to have an N-shaped cross-section.

Then, the press members 63 and 64 are further moved to approach each other. By moving the press members 63 and 64 to approach each other, the sheet member 3A is deformed to be narrower in the width of an N-shape in FIG. 16, and the first region A1 is deformed to cover the first string portion 41. The flat plates 61 and 62 restrict movement of the sheet member 3A in a vertical direction in FIG. 16. Here, since the sheet member consists of deformable fibers, the first side edge 31 is deformed to run upon and cover the first string portion 41 by way of a horizontal compression by the pressing members 63 and 64.

On the other hand, the second side edge 32 is deformed toward the flat plate 62, to be mutually alternating with the first side edge 31. As a result, the region B2 of the sheet member 3A in the vicinity of the first string portion 41 is deformed to run upon and cover the first string portion 41.

In the sheet member 3, the first string portion 41 is ultimately disposed midway between the flat plates 61 and 62, since a deforming force of the first folding portion 22 toward the flat plate 61 and a deforming force of the second folding portion toward the flat plate 62 balance out. The string-shaped member 4 is thus disposed in a substantially central portion of the absorbent core 2 and is covered by the first region.

3. Other Embodiments
3-1. Other Folding Portions
3-1-a. Dotted Line

Figure 17:
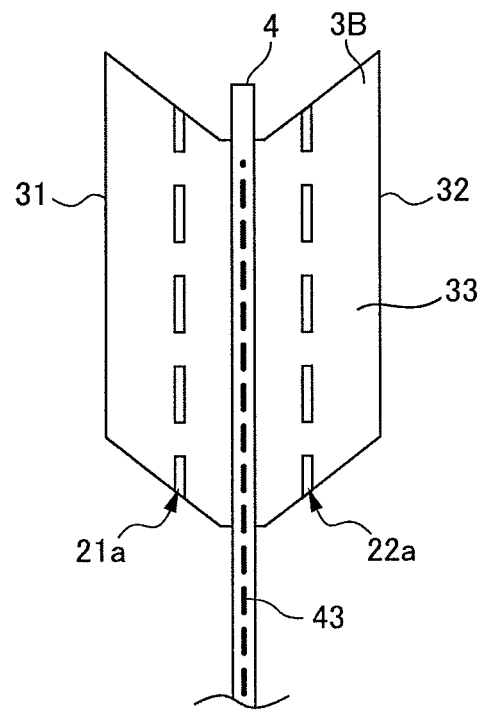
FIG. 17 is a diagram illustrating a modification of a sheet member according to another embodiment.

As described above, the number and shape of the folding portions are not particularly limited as long as the folding portions do not decrease the absorptive capacity of the sheet member. FIG. 17 is a plan view of the sheet member after forming the first folding portion and the second folding portion in a dotted line. As shown in FIG. 17, concave portions can be provided in a dotted line along the first direction as the folding portions 21a and 22a. By making the concave portion in a dotted line, the absorptive capacity of the sheet member can be increased when compared to a case where the entire folding portion is concave, while maintaining a function of a fold starting point. This is because a non-concave portion between dots that is not compressed has a lower density and a higher absorptive capacity than the concave portion.

3-1-b. Multiple Openings

Figure 18:
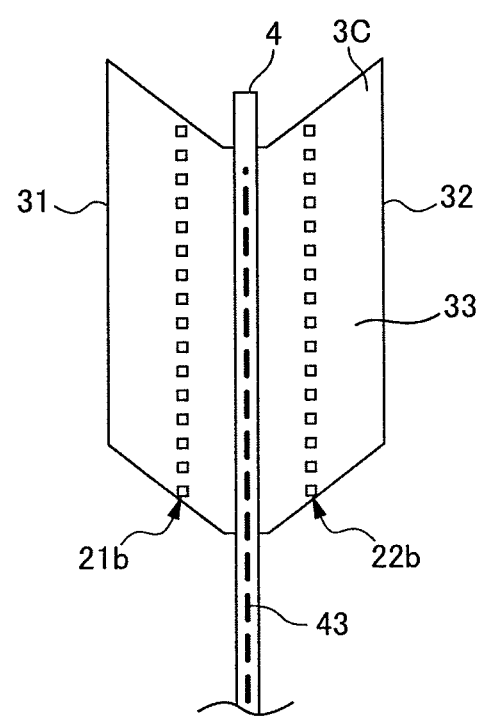
FIG. 18 is a diagram illustrating a modification of a sheet member according to another embodiment.

FIG. 18 is a plan view of the sheet member after forming the first folding portion and the second folding portion in consecutive openings. As shown in FIG. 18, the folding portions 21b and 22b can be configured to include multiple openings that are consecutively formed along the first direction. The multiple openings can be formed on the sheet member 3C by disposing a member including a plurality of pins in place of the projection of the creasing machine 50. The folding portions 21b and 22b are only required to induce a fold as a fold starting point, by changing the stiffness thereof from a portion adjacent thereto in the sheet member 3C. Therefore, the folding portion can be formed also by lowering the stiffness of the folding portions 21b and 22b more than that of the portion adjacent thereto, by providing multiple openings.

3-1-c. Transversal Line

Figure 19:
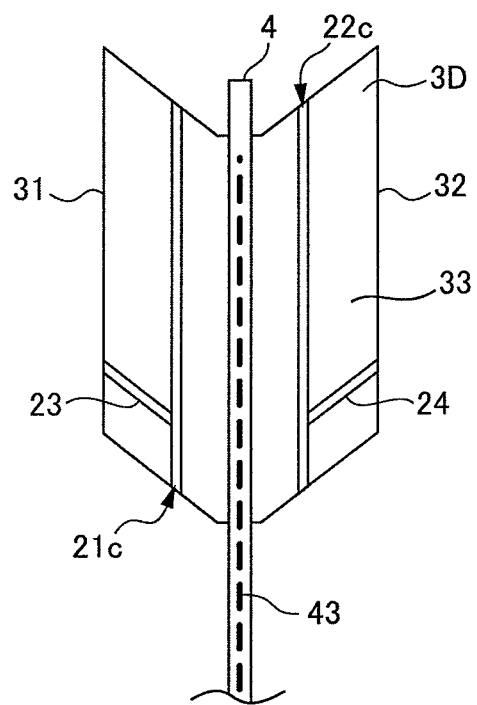
FIG. 19 is a diagram illustrating a modification of a sheet member according to another embodiment.

FIG. 19 is a plan view of the sheet member after forming a transversal line in the first folding portion and the second folding portion. As shown in FIG. 19, in addition to the folding portions 21c and 22c as in the first embodiment, concave portions 23 and 24 in a transversal line can be formed from the first folding portion 21c and the second folding portion 22c to the first side edge 31 and the second side edge 32, in a range of 5 to 70 degrees with respect to the second direction.

The transversal line can be formed either by forming a concave portion as in the first embodiment, or by increasing the density or stiffness of the sheet member 3D when compared to a region adjacent to transversal lines 23 and 24.

The sheet member 3D is compression-molded into the cylindrically-shaped absorbent core 2, and inserted into the vagina of a woman such that the first string portion is disposed inside the vagina and the second string portion is disposed outside the vagina. Menstrual blood runs inside a user's body and is first absorbed by a portion of the absorbent core closer to the vagina. By forming the transversal lines 23 and 24 in the sheet member 3D, menstrual blood absorbed by a portion of the absorbent core 2 disposed in a deep portion inside the vagina is held at an extremity by the transversal lines 23 and 24. When an amount of absorbed menstrual blood approaches or exceeds the maximum absorption amount of the portion of the absorbent core 2 disposed in a deep portion inside the vagina, the absorbed menstrual blood goes across the transversal lines 23 and 24 and is diffused into a portion of the absorbent core 2 disposed in a shallow portion inside the vagina. This allows the absorbent core 2 to absorb more menstrual blood, up to the maximum absorption amount thereof.

3-1-d. Partial Formation

FIG. 20 is a plan view of the sheet member on which a folding portion is partially formed. FIG. 21 is a plan view of the sheet member on which a partial folding portion is formed to incline toward the string-shaped member. As shown in FIGS. 20 and 21, the folding portions 21d, 22d, 21e, and 22e may be partially provided along the first direction, and may not be provided fully across the sheet members 3E and 3F in the first direction. By providing the folding portions 21d and 22d as in FIG. 20, the absorptive capacity of the sheet member can be increased when compared to a case where the entire folding portion is concave, while maintaining a function of a fold starting point. The folding portions 21e and 22e are inclined such that a portion closer to the second string portion 42 approaches the string-shaped member 4.

By making the folding portions 21e and 22e incline toward the string-shaped member 4, a pulling force can be concentrated in the string-shaped member 4 when a user pulls the string-shaped member 4 for removing the tampon 1 after use. Concentrating the pulling force in the string-shaped member 4 can avoid the tampon 1 from being inclined inside the vagina and decrease an uncomfortable feeling and an unpleasant feeling when removing.

3-2. Forming of Folding Portions by Heat Shrinkage

The sheet member 3 of the tampon 1 described in the first and the second embodiments can include a multi-layered absorbent layer. In addition, the sheet member can be covered by a covering sheet 7 consisting of a liquid permeable sheet, a liquid impermeable sheet or the like. As the liquid permeable sheet and the liquid impermeable sheet, a non-woven fabric consisting of PESB or PETSB singly, or mixed NB can be used.

The folding portions 21 and 22 of the tampons 1 and 1A can be formed by heat shrinkage, and not by forming a concave portion by the creasing machine 50. If the covering sheet 7 such as the liquid permeable sheet and the liquid impermeable sheet is made of a thermofusion material, fold starting points can be provided by heating regions in which the folding portions 21 and 22 are to be formed by the creasing machine 50. Here, a portion where the covering sheet 7, such as the liquid permeable sheet, and the liquid impermeable sheet for covering the sheet member overlap each other can be compressed for higher stiffness, and the sheet can be thermally fused.

In addition, in a case where an absorbent member is covered by the covering sheet 7, such as the liquid permeable sheet and the liquid impermeable sheet, which is a thermofusion material, and the folding portions are formed by heat shrinkage, the absorbent member is fixed to the liquid permeable sheet or the liquid impermeable sheet of the sheet member 3 by thermal fusion, thereby preventing the sheet member 3 from losing its shape and the absorbent member from delaminating. As a result, when removing of the tampon 1, this can lower a possibility of breakage of the liquid permeable sheet or the liquid impermeable sheet and prevent fibers of the absorbent member from remaining in the vagina.

3-3. Forming of Folding Portions by Multi-Layered Absorbent Layer

In the sheet member 3, a fold starting point can be formed on each of absorbent layers that are layered, by changing stiffness, density, basis weight and the like thereof. Alternatively, fold starting points can be formed at different positions on each of the absorbent layers and stacked to form a folding portion.

For example, in a case where the sheet member 3 is formed with 8 absorbent layers, fold starting points corresponding to the first folding portion and the second folding portion can be formed on two of the layers by an arbitrary method. The absorbent core 2 can be obtained by layering the absorbent layers, covering with the liquid permeable sheet or the liquid impermeable sheet, and then compressing.

The shape of the sheet member is not particularly limited. Although an arrowhead shape is shown in the present embodiments, the sheet member can have an arbitrary shape such as square, oval and the like, within the scope of the present invention.

The invention claimed is:

1. A tampon comprising:
   an absorbent core obtained by molding a sheet member into a cylindrical shape;
   a string-shaped member that is bound to the absorbent core and extends from one end of the absorbent core, wherein the string-shaped member includes a first string portion that is bound to a first surface of the sheet member constituting the absorbent core along a first direction, and a second string portion that extends from the sheet member;
   an opposing portion that is located on a second surface of the sheet member directly opposite a portion of the first surface on which the first string portion is bound;
   a first folding portion formed to one side of the first string portion in a second direction orthogonal to the first direction;
   a second folding portion formed to another side of the first string portion in the second direction;
   a first region of the sheet member that is between the first folding portion and an outer edge of the sheet member close to the first folding portion in the second direction; and
   a second region of the sheet member that is between the second folding portion and an outer edge of the sheet member close to the second folding portion in the second direction,
   wherein a distance between the first string portion and the first folding portion is not greater than a width of the first region in the second direction, and a distance between the first string portion and the second folding portion is not greater than a width of the second region in the second direction,
   wherein the first folding portion is a first concave portion, the second folding portion is a second concave portion, the first and second concave portions are formed by compressing the sheet member in the thickness direction, and both the first and second concave portions have a thickness smaller than that of a region adjacent to the first folding portion and the second folding portion,
   wherein a height of the first concave portion and a height of the second concave portion each are in a range of 1 to 3.2 mm, when an average thickness of the sheet member in a non-compressed state is in a range of 3.5 to 3.8 mm, and a width of the first concave portion and a width of the second concave portion each are in a range of 0.5 to 5 mm, and
   wherein the absorbent core is deformed so as to fold with the first folding portion and the second folding portion as fold starting points, and the first region or the second region is disposed to cover the first string portion, and molded into a cylindrical shape so as not to expose the first string portion and the opposing portion on the second surface of the sheet member.

2. The tampon according to claim 1,
   wherein the first folding portion and the second folding portion include a first concave portion and a second concave portion, respectively, formed so that a thickness of the sheet member is smaller in thickness than a region adjacent to the first folding portion and the second folding portion, and so as to concave at least one face of the sheet member in a thickness direction thereof.

3. The tampon according to claim 1,
   wherein the first concave portion and the second concave portion are formed on the first surface of the sheet member.

4. The tampon according to claim 1,
   wherein the first concave portion is provided on the first surface and the second concave portion is provided on the second surface which is opposite to the first surface.

5. The tampon according to claim 1,
   wherein the first folding portion and the second folding portion are formed at a predetermined distance away from the first string portion in the second direction, the predetermined distance being no greater than a quarter of an overall length of the sheet member in the second direction.

6. The tampon according to claim 3,
   wherein the sheet member is formed to have a W-shaped cross-section when viewed from a vertical surface in a longitudinal direction of a cylindrical shape.

7. The tampon according to claim 4,
   wherein the sheet member is formed to have an N-shaped cross-section when viewed from a vertical surface in the longitudinal direction of the cylindrical shape.

8. A tampon comprising:
   an absorbent core obtained by molding a sheet member into a cylindrical shape;
   a string-shaped member that is bound to the absorbent core and extends from one end of the absorbent core, wherein the string-shaped member includes a first string portion that is bound to a first surface of the sheet member constituting the absorbent core along a first direction so as to cover more than half of a thickness of the first string portion, and a second string portion that extends from the sheet member;
   a sewing thread disposed in the first string portion and the second string portion;
   an opposing portion located on a second surface of the sheet member directly opposite a portion of the first surface on which the first string portion is bound and sewn;
   a first folding portion formed to one side of the first string portion in a second direction orthogonal to the first direction;
   a second folding portion formed to another side of the first string portion in the second direction;
   a first region of the sheet member that is between the first folding portion and an outer edge of the sheet member close to the first folding portion in the second direction; and a second region of the sheet member that is between the second folding portion and an outer edge of the sheet member close to the second folding portion in the second direction, wherein a distance between the first string portion and the first folding portion is not greater than a width of the first region in the second direction, and a distance between the first string portion and the second folding portion is not greater than a width of the second region in the second direction, wherein the first folding portion is a first concave portion, the second folding portion is a second concave portion, the first and second concave portions are formed by compressing the sheet member in the thickness direction, and both the first and second concave portions have a thickness smaller than that of a region adjacent to the first folding portion and the second folding portion, wherein a height of the first concave portion and a height of the second concave portion each are in a range of 1 to 3.2 mm, when an average thickness of the sheet member in a non-compressed state is in a range of 3.5 to 3.8 mm, and a width of the first concave portion and a width of the second concave portion each are in a range of 0.5 to 5 mm, and wherein the absorbent core is deformed so as to fold with the first folding portion and the second folding portion as fold starting points, and the first region or the second region is disposed to cover the first string portion, and molded into a cylindrical shape so as not to expose the first string portion and the opposing portion on the second surface of the sheet member.

9. The tampon according to claim 8, wherein the sheet member is formed into an arrowhead shape so that the second string portion extends from a front edge of the arrowhead shape, the string-shaped member further comprises a projecting portion that projects from the first string portion and extends from a tail edge of the arrowhead shape, and the projecting portion is either disposed inside the absorbent core or compressed along a surface of the absorbent core, when the absorbent core is molded.

* * * * *